(12) United States Patent　(10) Patent No.: US 8,165,695 B2
DiUbaldi et al.　(45) Date of Patent: Apr. 24, 2012

(54) SYSTEM AND METHOD FOR SELECTIVELY STIMULATING DIFFERENT BODY PARTS

(75) Inventors: Anthony DiUbaldi, Jackson, NJ (US); Michael R. Tracey, Branchburg, NJ (US)

(73) Assignee: Ethicon, Inc., Somerville, NJ (US)

( * ) Notice: Subject to any disclaimer, the term of this patent is extended or adjusted under 35 U.S.C. 154(b) by 1598 days.

(21) Appl. No.: 11/343,627

(22) Filed: Jan. 31, 2006

(65) Prior Publication Data

US 2006/0195153 A1　Aug. 31, 2006

Related U.S. Application Data

(63) Continuation-in-part of application No. 11/146,522, filed on Jun. 7, 2005, now Pat. No. 7,979,137, which is a continuation-in-part of application No. 11/043,830, filed on Jan. 26, 2005, now abandoned.

(60) Provisional application No. 60/543,722, filed on Feb. 11, 2004.

(51) Int. Cl.
*A61N 1/00*　(2006.01)

(52) U.S. Cl. ........................................................ 607/71

(58) Field of Classification Search ................. 607/1–3, 607/40, 41, 115–18, 71; 600/372, 373
See application file for complete search history.

(56) References Cited

U.S. PATENT DOCUMENTS

| | | |
|---|---|---|
| 3,683,915 A | 8/1972 | Voss |
| 3,902,502 A | 9/1975 | Liss et al. |
| 3,933,147 A | 1/1976 | DuVall et al. |
| 3,941,136 A | 3/1976 | Bucalo |
| 4,406,288 A | 9/1983 | Horwinski et al. |
| 4,537,195 A * | 8/1985 | McDonnell ..................... 607/46 |

(Continued)

FOREIGN PATENT DOCUMENTS

EP　0783267 B1　2/1999

(Continued)

OTHER PUBLICATIONS

Walter et al, "Evaluation of a 316LVM Woven Eye Electrode for Direct Bladder Stimulation", *Engineering in Medicine and Biology Society 1991*, vol. 13:1991, Proceedings of the Annual International Conference of the IEEE Orlando, FL, USA, Oct. 31-Nov. 3, 1991, New York, NY, USA, IEEE, US, Oct. 31, 1991, pp. 1853-1854.

(Continued)

*Primary Examiner* — Eric D. Bertram
(74) *Attorney, Agent, or Firm* — Cheryl F. Cohen, LLC

(57) ABSTRACT

A device and method is provided for transdermally stimulating selected body parts of a mammal. The device includes a first waveform generator adapted to generate a first waveform having a first frequency capable of stimulating a first predetermined body part, a second waveform generator adapted to generate a carrier waveform having a second frequency capable of passing through tissue of the mammal, and a third waveform generator adapted to generate a third waveform having a third frequency different from and out of phase with that of the first waveform, and capable of stimulating a second predetermined body part. The device further includes a modulation device electrically coupled to the first, second and third waveform generators and adapted to modulate the carrier, first, and third waveforms to create a modulated signal package, and a first electrode electrically coupled to the modulation device and positioned substantially adjacent to the skin of the mammal, and adapted to apply the modulated signal package thereto.

15 Claims, 14 Drawing Sheets

U.S. PATENT DOCUMENTS

| | | |
|---|---|---|
| 4,719,922 A | 1/1988 | Padjen et al. |
| 4,909,255 A * | 3/1990 | Farin ............... 607/67 |
| 4,989,605 A | 2/1991 | Rossen |
| 5,167,237 A | 12/1992 | Rabin et al. |
| 5,350,414 A * | 9/1994 | Kolen ............... 607/62 |
| 5,458,630 A | 10/1995 | Hoegnelid et al. |
| 5,464,434 A | 11/1995 | Alt |
| 5,476,481 A | 12/1995 | Schondorf |
| 5,487,759 A | 1/1996 | Bastyr et al. |
| 5,556,421 A | 9/1996 | Prutchi et al. |
| 5,558,640 A | 9/1996 | Pfeiler et al. |
| 5,562,717 A | 10/1996 | Tippey et al. |
| 5,617,876 A | 4/1997 | van Duyl |
| 5,645,062 A | 7/1997 | Anderson et al. |
| 5,702,428 A * | 12/1997 | Tippey et al. ............ 607/41 |
| 5,722,996 A | 3/1998 | Bonnet et al. |
| 5,730,125 A | 3/1998 | Prutchi et al. |
| 5,735,887 A | 4/1998 | Barreras, Sr. et al. |
| 5,791,344 A | 8/1998 | Schulman et al. |
| 5,851,223 A * | 12/1998 | Liss et al. ............ 607/46 |
| 5,902,329 A | 5/1999 | Hoffmann et al. |
| 5,984,854 A | 11/1999 | Ishikawa et al. |
| 5,993,414 A | 11/1999 | Haller |
| 6,092,530 A | 7/2000 | Weissman et al. |
| 6,099,479 A | 8/2000 | Christopherson et al. |
| 6,155,267 A | 12/2000 | Nelson |
| 6,164,284 A | 12/2000 | Schulman et al. |
| 6,167,304 A | 12/2000 | Loos |
| 6,183,461 B1 | 2/2001 | Matsuura et al. |
| 6,199,575 B1 | 3/2001 | Widner |
| 6,205,359 B1 | 3/2001 | Boveja |
| 6,221,024 B1 | 4/2001 | Miesel |
| 6,231,516 B1 | 5/2001 | Keilman et al. |
| 6,240,317 B1 | 5/2001 | Villaseca et al. |
| 6,263,246 B1 | 7/2001 | Goedeke et al. |
| 6,285,897 B1 | 9/2001 | Kilcoyne et al. |
| 6,298,272 B1 | 10/2001 | Peterfeso et al. |
| 6,330,885 B1 | 12/2001 | Weissman et al. |
| 6,354,991 B1 | 3/2002 | Gross et al. |
| 6,360,129 B1 | 3/2002 | Ley et al. |
| 6,366,814 B1 | 4/2002 | Boveja et al. |
| 6,377,853 B1 | 4/2002 | Malaney et al. |
| 6,384,353 B1 | 5/2002 | Huang et al. |
| 6,402,689 B1 | 6/2002 | Scarantino et al. |
| 6,404,204 B1 | 6/2002 | Farruggia et al. |
| 6,413,393 B1 | 7/2002 | Van Antwerp et al. |
| 6,432,050 B1 | 8/2002 | Porat et al. |
| 6,438,407 B1 | 8/2002 | Ousdigian et al. |
| 6,442,413 B1 | 8/2002 | Silver |
| 6,443,883 B1 | 9/2002 | Ostrow et al. |
| 6,447,462 B1 | 9/2002 | Wallace et al. |
| 6,459,933 B1 | 10/2002 | Lurie et al. |
| 6,471,645 B1 | 10/2002 | Warkentin et al. |
| 6,497,655 B1 | 12/2002 | Linberg et al. |
| 6,505,074 B2 | 1/2003 | Boveja et al. |
| 6,535,766 B1 | 3/2003 | Thompson et al. |
| 6,560,490 B2 | 5/2003 | Grill et al. |
| 6,567,706 B2 | 5/2003 | Bar-Or et al. |
| 6,652,449 B1 | 11/2003 | Gross et al. |
| 6,662,052 B1 | 12/2003 | Sarwal et al. |
| 6,668,191 B1 | 12/2003 | Boveja |
| 6,701,185 B2 | 3/2004 | Burnett et al. |
| 6,712,772 B2 | 3/2004 | Cohen et al. |
| 6,751,501 B1 | 6/2004 | Schuler et al. |
| 6,836,684 B1 | 12/2004 | Rijkhoff et al. |
| 6,862,480 B2 | 3/2005 | Cohen et al. |
| 6,879,859 B1 | 4/2005 | Boveja |
| 6,907,293 B2 | 6/2005 | Grill et al. |
| 7,047,078 B2 | 5/2006 | Boggs, II et al. |
| 7,062,330 B1 | 6/2006 | Boveja et al. |
| 7,387,603 B2 | 6/2008 | Gross et al. |
| 7,427,280 B2 | 9/2008 | Gerber |
| 7,599,736 B2 | 10/2009 | DiLorenzo |
| 7,676,271 B2 | 3/2010 | Wahlstrand et al. |
| 7,815,895 B2 | 10/2010 | Katagiri et al. |
| 2001/0018606 A1 | 8/2001 | Ingle et al. |
| 2001/0025137 A1 | 9/2001 | Webb et al. |
| 2001/0051768 A1 | 12/2001 | Schulman et al. |
| 2002/0001870 A1 | 1/2002 | Oda et al. |
| 2002/0011592 A1 | 1/2002 | Matsuo |
| 2002/0026141 A1 | 2/2002 | Houben et al. |
| 2002/0026244 A1 | 2/2002 | Trieu |
| 2002/0082480 A1 | 6/2002 | Riff et al. |
| 2002/0103514 A1 | 8/2002 | Abrahamson |
| 2002/0107540 A1 | 8/2002 | Whalen et al. |
| 2002/0111542 A1 | 8/2002 | Warkentin et al. |
| 2002/0133196 A1 | 9/2002 | Thompson |
| 2002/0151816 A1 | 10/2002 | Rich et al. |
| 2003/0004403 A1 | 1/2003 | Drinan et al. |
| 2003/0004553 A1 | 1/2003 | Grill et al. |
| 2003/0162021 A1 | 8/2003 | Van Heerden et al. |
| 2003/0212305 A1 | 11/2003 | Anderson et al. |
| 2003/0220669 A1 | 11/2003 | Shealy |
| 2003/0233137 A1 | 12/2003 | Paul |
| 2004/0068203 A1 | 4/2004 | Gellman et al. |
| 2004/0236194 A1 | 11/2004 | Meyer |
| 2005/0177067 A1 | 8/2005 | Tracey et al. |
| 2005/0277998 A1 | 12/2005 | Tracey et al. |
| 2006/0111756 A1 | 5/2006 | Chang |
| 2006/0167500 A1 | 7/2006 | Towe et al. |
| 2006/0178703 A1 | 8/2006 | Huston |
| 2006/0195146 A1 | 8/2006 | Tracey et al. |
| 2006/0195153 A1 | 8/2006 | DiUbaldi |
| 2006/0229688 A1 | 10/2006 | McClure |
| 2006/0247721 A1 | 11/2006 | Maschino |
| 2007/0162085 A1 | 7/2007 | DiLorenzo |
| 2007/0167990 A1 | 7/2007 | Mangrum et al. |
| 2007/0219606 A1 | 9/2007 | Moreci et al. |
| 2007/0233204 A1 | 10/2007 | Lima et al. |
| 2007/0260288 A1 | 11/2007 | Gross |
| 2008/0132962 A1 | 6/2008 | DiUbaldi et al. |
| 2008/0132969 A1 | 6/2008 | Bennett et al. |
| 2008/0147146 A1 | 6/2008 | Wahlgren et al. |
| 2008/0161874 A1 | 7/2008 | Bennett et al. |
| 2008/0293830 A1 | 11/2008 | Katagiri et al. |
| 2009/0005713 A1 | 1/2009 | Podrazhansky et al. |
| 2009/0048642 A1 | 2/2009 | Goroszeniuk |
| 2009/0054952 A1 | 2/2009 | Glukhovsky et al. |
| 2009/0062874 A1 | 3/2009 | Tracey et al. |
| 2009/0132018 A1 | 5/2009 | DiUbaldi et al. |
| 2009/0157149 A1 | 6/2009 | Wahlgren et al. |
| 2009/0187230 A1 | 7/2009 | Dilorenzo |
| 2010/0042018 A1 | 2/2010 | Kleinsinger |
| 2010/0042180 A1 | 2/2010 | Mueller et al. |
| 2010/0076533 A1 | 3/2010 | Dar et al. |

FOREIGN PATENT DOCUMENTS

| | | |
|---|---|---|
| EP | 1048264 A1 | 11/2000 |
| JP | 2001-259047 | 9/2001 |
| WO | WO 90/14127 A | 11/1990 |
| WO | WO 97/18856 A1 | 5/1997 |
| WO | WO 97/39796 A1 | 10/1997 |
| WO | WO 99/55411 A2 | 11/1999 |
| WO | WO 0033738 A1 | 5/2000 |
| WO | WO 00/33065 A1 | 6/2000 |
| WO | WO 01/49369 A1 | 7/2001 |
| WO | WO 01/56633 A2 | 8/2001 |
| WO | WO 02/22008 A1 | 3/2002 |
| WO | WO 02/27294 A1 | 4/2002 |
| WO | WO 02/058551 A3 | 8/2002 |
| WO | WO 02/062215 A2 | 8/2002 |
| WO | WO 03/015625 A1 | 2/2003 |
| WO | WO 03/020364 A2 | 3/2003 |
| WO | WO 03/030733 A | 4/2003 |
| WO | WO 03/071944 A1 | 9/2003 |
| WO | WO 2004/050172 A | 6/2004 |
| WO | WO 2005/002663 A2 | 1/2005 |
| WO | WO 2005/079909 | 9/2005 |
| WO | WO 2007/092301 A2 | 8/2007 |

OTHER PUBLICATIONS

Siwapornsathain, E. et al., "Telemetry and Sensor Platform for Ambulatory Urodynamics", Proceedings of the 2nd Annual International IEEE-EMBS Special Topica Conference on Microtechnologies in Medicine & Biology, Madison, WI, May 2002.

Rousche, P.J. et al. "Flexible Polyimide-Based Intracortical Electrode Arrays with Bioactive Capability", IEEE Transactions on Biomedical Engineering, vol. 48, No. 3 (2001).

Becker, T.J. "CardioMEMS Moves Closer to Commercializing Its Innovative Heart Sensors", (1905) ATDC News & Information, Georgia Institute of Technology.

Voskerician, G. et al., "Biocompatibility and biofouling of MEMS drug delivery devices" Biomaterials, 24, 1959-1967 (2003).

Fiber Optic Sensors, Product Datasheet FOP-M Pressure sensor (undated).

Chappell, J. Electronic News—Ambient Intelligence (2002).

Copending, co-owned U.S. Appl. No. 60/543,722, filed Feb. 11, 2004.

Copending, co-owned U.S. Appl. No. 11/043,830, filed Jan. 26, 2005.

Copending, co-owned U.S. Appl. No. 11/146,522, filed Jun. 7, 2005.

Copending, co-owned U.S. Appl. No. 11/497,861, filed Aug. 2, 2006.

Copending, co-owned U.S. Appl. No. 12/661,949, filed Mar. 26, 2010.

Copending, co-owned U.S. Appl. No. 13/094,644, filed Apr. 26, 2011.

Copending, co-owned U.S. Appl. No. 11/344,285, filed Jan. 31, 2006.

Copending, co-owned U.S. Appl. No. 61/211,197, filed Mar. 27, 2009.

Rosell, J. et al., "Skin Impedance from 1 Hz to 1 MHz," IEEE Transactions on Biomedical Engineering, vol. 35, No. 8, Aug. 1988.

Reilly, J. Patrick, "Electrical Stimulation and Electropathology," Cambridge University Press (1992).

Frost & Sullivan Report (2002).

Junge et al., "Titanium Coating of a Polypropylene Mesh for Hernia Repair: Effect on Biocompatibiity," Hernia vol. 6, No. 9, pp. 115-119, pub. on line Dec. 4, 2004.

International Search Report dated Sep. 2, 2010 for International Application No. PCT/US2010/028690 (8 pages).

Reilly, J. Patrick, "Electrical Stimulation and Electropathology," Cambridge University Press (1992); pp. 120-129; 190-205; 252-261; 308-325; 447-459.

* cited by examiner

FIG. 12a
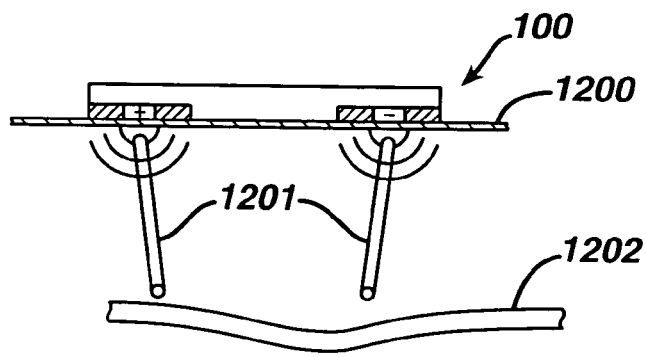
FIG. 12b
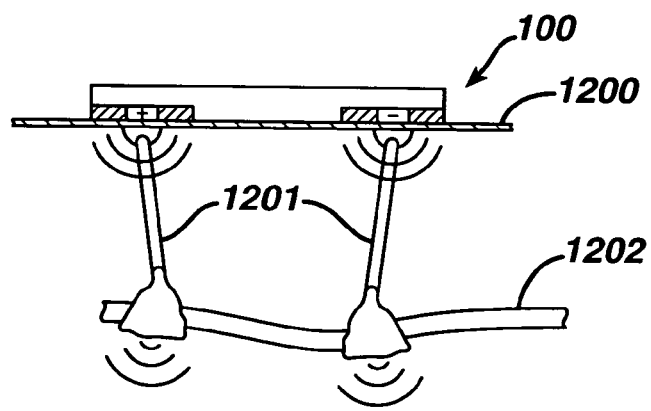
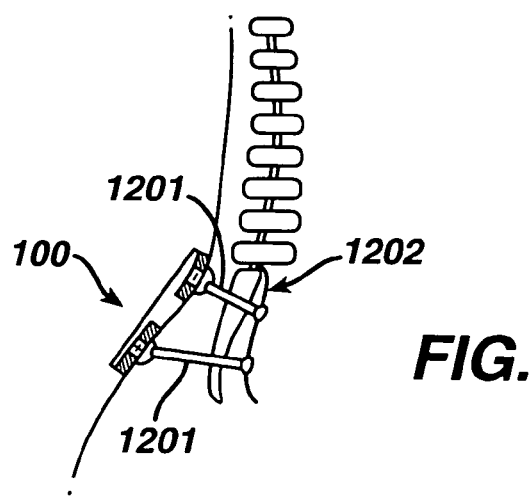
FIG. 12c

SYSTEM AND METHOD FOR SELECTIVELY STIMULATING DIFFERENT BODY PARTS

CROSS-REFERENCE TO RELATED APPLICATIONS

The present application a continuation-in-part of U.S. patent application Ser. No. 11/146,522, filed on Jun. 7, 2005, now U.S. Pat. No.7,979,137 which is a continuation-in-part of co-pending U.S. patent application Ser. No. 11/043,830, filed on Jan. 26, 2005, now abandoned which claims priority to U.S. provisional patent application Ser. No. 60/543,722, filed on Feb. 11, 2004.

BACKGROUND OF THE INVENTION

1. Field of the Invention

The present invention relates generally to devices and methods for selectively stimulating parts of the body, and more particularly to devices and method for selectively stimulating various nerves or selectively applying electrical stimulation to various other body parts.

2. Background Discussion

Women account for more than 11 million incontinence cases. One type of incontinence is stress urinary incontinence (SUI), where women experience involuntary loss of urine during normal daily activities and movements, such as laughing, coughing, sneezing and regular exercise. SUI may be caused by a functional defect of the tissue or ligaments connecting the vaginal wall with the pelvic muscles and pubic bone. Common causes include repetitive straining of the pelvic muscles, childbirth, loss of pelvic muscle tone, and estrogen loss. Such a defect results in an improperly functioning urethra. Unlike other types of incontinence, SUI is not a problem of the bladder.

Where stress incontinence is typically a result of an anatomical defect, another form of incontinence, urge incontinence, appears to be neurologically based and generally revealed as detrusor muscle instability or "bladder spasms." As such it is usually not conducive to surgical correction. Urge incontinence may or may not result in urine leakage, but both conditions otherwise have similar symptoms and similar forms of treatment, which generally include a combination of behavioral modification (learned strategies for reducing the urge sensation, scheduled voiding, avoidance of bladder-stimulating substances such as caffeine, and pelvic muscle exercises, with or without biofeedback) and drug therapy (typically anticholinergeic agents such as oxybutynin or tolterodine). These treatments require life-long therapy. Unfortunately, behavioral modification requires continuous effort to maintain results and the available drugs have significant side effects for many patients causing 80% to discontinue therapy within a year. The alternative therapy is to modify lifestyle to accommodate the condition—frequent urination to avoid "accidents" and wearing protective pads or undergarments, depending on the severity of the condition.

Another approach for treatment is stimulation of the sacral and/or pudendal nerve. The sacral spinal nerve roots separate in pairs to exit laterally through the nerve root foramina. The main destinations for these roots are the sacral plexus. Nerves from this plexus provide the motor and sensory innervation of the lower limbs and pelvic organs. Specifically, the sacral plexus splits into five sacral nerve pair, sacral spinal nerves S1 to S5. These nerves supply the thighs and lower parts of the legs, the feet, most of the external genital organs, and the area around the anus. The pudendal nerve is the largest branch of the pudendal plexus and is composed of somatosensory, somatomotor and autonomic elements derived from the anterior primary divisions of the second, third and fourth sacral nerves. The pudendal nerve affects the function of the bladder, urethral sphincter and genitals. Lower branches of the pudendal nerve contribute to peristalsis of the colon and anal sphincter contraction force. The pudendal nerve is closer to the bladder, and its stimulation innervates the bladder, thus eliminating or lessening its contractions. At least one known commercial device stimulates the sacral nerve through a needle extended into the sacral nerve bundle. This device, however, supplies a continuous signal to provide constant stimulation of the nerve. Various drawbacks of this device include its invasive nature, and unwanted stimulation effects on other areas of the body, since the sacral nerve as a whole is being stimulated and multiple other areas of the body are innervated by such stimulation (i.e., resulting in leg twitches or the like).

A company called Advanced Bionics has an implantable stimulation device that targets the pudendal nerve specifically rather than the sacral nerve. This device is implanted in the vicinity of the pudendal nerve, but also is invasive and supplies a constant signal as described above and therefore, has the same drawbacks.

In addition to incontinence, women can suffer from other diseases as well, often simultaneously with incontinence. Interstitial cystitis is a chronic bladder condition involving an inflamed or irritated bladder wall. Patients with this condition may experience mild discomfort, pressure, tenderness, or intense pain in the bladder and surrounding pelvic area. Other symptoms may include an urgent need to urinate (urgency), frequent need to urinate (frequency), or a combination of these symptoms. The inflammation can lead to scarring and stiffening of the bladder, less bladder capacity (the bladder is able to hold less urine), and pinpoint bleeding in the bladder lining. In rare cases, ulcers form in the bladder lining. Of the more than 700,000 Americans estimated to have interstitial cystitis, about 90 percent are women.

Treatments for interstitial cystitis include oral medicines, such as aspirin, ibuprofen, other painkillers, antidepressants and antihistamines. Another treatment is bladder instillation (a bladder wash or bath) in which the bladder is filled with a solution that is held for varying periods of time before being emptied. These treatments require life-long therapy. Sacral nerve stimulation implants are also used for the treatment of interstitial cystitis, but, as stated previously, its invasive nature and unwanted stimulation effects on other areas of the body make this treatment undesirable. Surgery, considered a treatment of last resort, does not necessarily improve symptoms.

Other diseases that may occur simultaneously with urinary incontinence include fecal and anal incontinence. Fecal incontinence is the inability to control the bowels, and can have several causes with constipation being the most common. Fecal incontinence can also be caused by injury to one or both of the ring-like muscles at the end of the rectum called the anal internal and/or external sphincters. In women, the damage often happens when giving birth. Hemorrhoid surgery can damage the sphincters as well. Fecal incontinence can also be caused by damage to the nerves that control the anal sphincters or to the nerves that sense stool in the rectum. Nerve damage can also be caused by childbirth, a long-term habit of straining to pass stool, stroke, and diseases that affect the nerves, such as diabetes and multiple sclerosis. In addition, rectal surgery, radiation treatment, and inflammatory bowel disease can cause scarring that makes the walls of the rectum stiff and less elastic. Abnormalities of the pelvic floor, which is typically caused by childbirth, can also lead to fecal incontinence. Examples of some abnormalities are decreased perception of rectal sensation, decreased anal canal pressures, decreased squeeze pressure of the anal canal, impaired anal sensation, a dropping down of the rectum (rectal prolapse), protrusion of the rectum through the vagina (rectocele), and/or generalized weakness and sagging of the pelvic floor. Treatment depends on the cause and severity of fecal incontinence, and may include dietary changes, medication, bowel training, or surgery. A last resort is a colostomy, which is the surgical creation of an opening between the large intestine and the abdominal wall. More than one treatment may be necessary for successful control since continence is a complicated chain of events.

One type of treatment typically cannot be used to treat the different conditions described above, and, as indicated above, many of the known treatments are invasive or have other negative side effects. Accordingly, what is needed is an improved device and method for simultaneously treating different diseases or conditions.

SUMMARY OF THE INVENTION

The present invention provides a system and method for transcutaneously stimulating multiple selected body parts of a mammal.

One transcutaneous electrical stimulation device provided herein includes a first waveform generator adapted to generate a first waveform having a first frequency capable of stimulating a first predetermined body part, a second waveform generator adapted to generate a carrier waveform having a second frequency capable of passing through tissue of the mammal, and a third waveform generator adapted to generate a third waveform having a third frequency different from and out of phase with that of the first waveform, and capable of stimulating a second predetermined body part. The device further includes a modulation device electrically coupled to the first, second and third waveform generators and adapted to modulate the carrier, first, and third waveforms to create a modulated signal package. and a first electrode electrically coupled to the modulation device and positioned substantially adjacent to the skin of the mammal, and adapted to apply the modulated signal package thereto.

The first, second, and third waveform generators and the electrode may be positioned within a patch device having an adhesive thereon for securing the patch to the skin, and the patch may further be positioned substantially in the abdominal or sacral regions of the mammal's body.

According to one embodiment, the device further includes a return electrode for receiving the signal package, wherein the first electrode and return electrode are both positioned external of and substantially adjacent to the skin of the mammal, and relative to each other such that the applied signal package may pass from the first electrode to the return electrode substantially without passing through tissue of the mammal. The first and second predetermined body parts may be different nerves of different branches of a given nerve, and may be the bladder and genitals respectively.

Further, the first waveform may have a frequency of approximately 20 Hz, the third waveform may have a frequency of approximately 10 Hz and the second carrier waveform may have a frequency of approximately 10-400 KHz. In yet another embodiment, the first and third waveforms are square waves and the second carrier waveform is a sinusoidal wave.

In an alternate embodiment, the device further includes a fourth waveform generator electrically coupled to the modulation device and adapted to generate a fourth carrier waveform having a frequency different than the second carrier waveform, wherein the modulation device further modulates the second carrier waveform to create the modulated signal package.

The modulation device may further include first, second and third modulators, wherein the first modulator modulates the first waveform and second carrier waveform to create a first modulated signal, and the second modulator modulates the third waveform and fourth carrier waveform to create a second modulated signal, and wherein the third modulator modulates the first and second modulated signals to create the modulated signal package. Alternatively, the modulation device may further include first and second modulators, wherein the first modulator modulates the first waveform and second carrier waveform to create a first modulated signal, and wherein the second modulator modulates the first modulated signal, third waveform, and fourth carrier waveform to create the modulated signal package, and wherein the fourth waveform generator generates the fourth waveform only during periods of inactivity of the first modulated signal.

The present invention also provides a transcutaneous electrical stimulation device for stimulating a plurality of different selected nerves or nerve branches of a mammal. The device includes a first waveform generator adapted to generate a first waveform having a first frequency capable of stimulating a first predetermined nerve or nerve branch, a second waveform generator adapted to generate a second carrier waveform having a second frequency capable of passing through tissue of the mammal, and a third waveform generator adapted to generate a third waveform having a third frequency different from and out of phase with that of the first frequency and capable of stimulating a second predetermined nerve or nerve branch. The device further includes a modulation device electrically coupled to the first, second and third waveform generators and adapted to modulate the second carrier waveform with the first and third waveforms to create a modulated signal package, and an electrode electrically coupled to the modulation device and positioned substantially adjacent to the skin of the mammal, and adapted to apply the modulated signal package thereto. This embodiment may also include any of the variation described above.

In addition, the present invention provides a method for transcutaneously and selectively stimulating more than one body part within a mammal. The method includes identifying a first and second internal body parts for selective stimulation, generating a first waveform having a frequency capable of stimulating the first identified body part, generating a second carrier waveform having a frequency capable of passing through tissue of said mammal to reach the first and second identified body parts, generating a third waveform having a frequency capable of stimulating the second identified body part, the third waveform being generated out of phase with the first waveform, modulating the first, second carrier, and third waveforms to create a modulated signal package, and applying the modulated signal package substantially to a skin surface of the mammal.

The modulating step may further include first modulating the first waveform and second carrier waveform to create a first modulated signal, and subsequently modulating the first modulated signal with the third waveform. In alternate embodiment the method further includes generating a fourth carrier waveform having a frequency different than the second carrier waveform, wherein the modulating step comprises the steps of modulating the first waveform and second carrier waveform to create a first modulated signal, and modulating the third waveform and fourth carrier waveform to create a second modulated signal.

In yet another embodiment, the modulating step further includes modulating the first and second modulated signals to create the modulated signal package.

BRIEF DESCRIPTION OF THE DRAWINGS

FIGS. 2a and 2b illustrates exemplary waveforms generated by the devices of FIGS. 1 and 1a;

FIGS. 12a-c illustrate use of the transdermal transmission device in connection with a conductive gel tract.

DETAILED DESCRIPTION OF THE INVENTION

Figure 1:
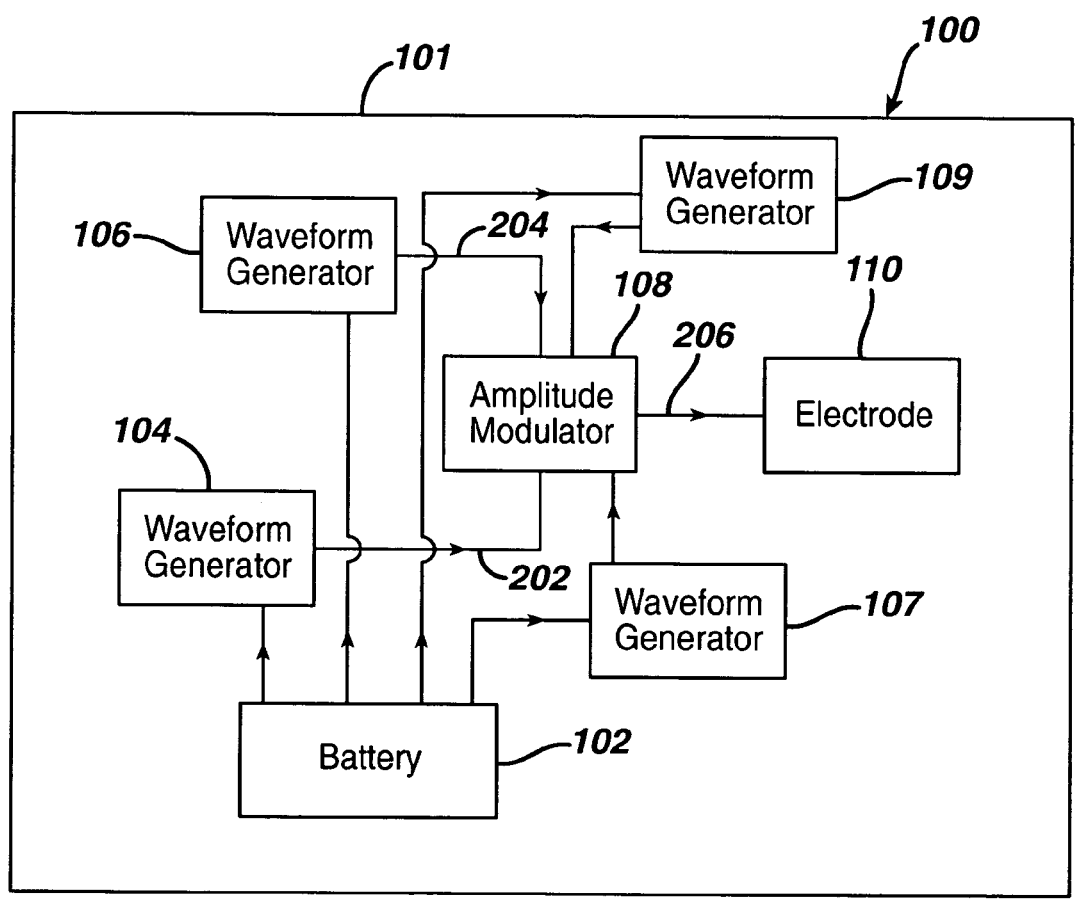
FIGS. 1 and 1a are schematic illustrations of transdermal transmission devices according to selected embodiments of the present invention.

Before explaining the present invention in detail, it should be noted that the invention is not limited in its application or use to the details of construction and arrangement of parts illustrated in the accompanying drawings and description. The illustrative embodiments of the invention may be implemented or incorporated in other embodiments, variations and modifications, and may be practiced or carried out in various ways. For example, although the present invention is described in detail in relation to nerve stimulation in females, it is to be understood that it can be readily adapted for use in males, and children as well as adults. The inventive principles, apparatus and methods disclosed herein may also have application for stimulating various other nerves, either independently or simultaneously, such as stimulation of nerves during labor and delivery, or selectively stimulating branches of a given nerve bundle to selectively address different patient conditions. Thus, the present invention can, for example, be used to selectively treat or affect one or more of the following conditions simultaneously: stress urinary incontinence, anal and fecal incontinence, sexual dysfunction, interstitial cystitis, chronic pain such as but not limited to pelvic pain, nocturia, and gastrointestinal disorders such as but not limited to gastric pacing. Finally, the present invention as described herein can also be used to stimulate body parts other than nerves, such as glands that secrete hormones, and large muscle groups, such as biceps muscle stimulation associated with physical therapy.

One unique aspect of the invention described herein is the manner in which the nerve(s) or other body parts are stimulated, which is transdermally rather than via a needle or other invasive element inserted within the body in close proximity to the nerve. This has obvious advantages in comfort for the patient, but also eliminates the surgical risk of mistakenly injuring other nerves or vessels. The system provides direct, but preferably selective stimulation to a nerve or the like that may be, if desired, controlled in part based on biofeedback data corresponding to physiological conditions sensed in the body, such as bladder contractions.

With regard to its application for stimulating nerves, an underlying principal of its operation is the fact that nerves within the body can be selectively targeted for stimulation without affecting adjacent neurons. As is well known to those skilled in the art, bioelectric potentials are produced as a result of electrochemical activity of excitable cells found within nervous system tissue. These excitable cells exist in two electrical states, resting potential or action potential. Cells remain in the resting potential state until adequate stimulus is provided to cause the cell to reach the action or threshold potential, at which time the nerve "fires," and the action potential travels at a constant conduction velocity unattenuated along the cell membranes. This all-or-nothing response of the action potential causes the cell's membrane potential to go through a characteristic repeatable cycle, where the potential first goes from the negative resting potential, to a positive action potential, and then back down to the negative resting potential again all within approximately 1 ms. The response remains the same regardless of the magnitude of the stimulus, so long as it exceeds the threshold potential.

As is also well known, when an excitable cell membrane has an action potential response (from an adequate stimulus), its ability to respond to a second stimulus is significantly altered. During the initial, depolarizing portion of the action potential, the cell membrane cannot respond to additional stimulus regardless of its intensity. This period is referred to as the absolute refractory period. Immediately following the absolute refractory period is the relative refractory period where the cell membrane can respond only to intense stimulation. The existence of the absolute and relative refractory periods results in an upper frequency limit at which a cell can be repeatedly discharged. Thus, neurons can be seen as frequency dependent devices. The frequency dependent component of the neuron depends on its total capacitance, which will vary from neuron to neuron and will be a function of its length, diameter, coating (myelination) and the permeativity of the dielectric medium. In other words, for any given dielectric medium, varying either the length or diameter of the neuron, or its myelination, will vary its total capacitance.

Since neurons in the human body do vary greatly in diameter, length and myelination, the capacitance and conduction velocity (operating frequency) for these neurons vary as well. Using these differences in physical characteristics of adjacent neurons, selected nerves can be targeted for stimulation without affecting adjacent neurons. That is, selective neural stimulation can be achieved by characterizing the frequency response (capacitance) of adjacent neurons, and tuning the stimulation frequency to an area of no-overlap. For example, consider two adjacent neurons, where neuron A has a frequency band of operation from 0-20 Hz, and neuron B has a frequency band of operation from 20-30 Hz. Thus, within the frequency band of 20-30 Hz, neuron B can be selectively stimulated with no effect on neuron A. Further, neuron A can be selectively stimulated even in an overlapping frequency range if stimulation is applied during neuron B's absolute refractory period, during which no amount of stimulation will cause neuron B to fire as discussed above, or if the stimulation is less than the magnitude required to cause stimulation during the relative refractory period. As described further below, these principles can be applied to achieve selective stimulation of two or more nerves within the body.

As indicated above, it is known that surface electrodes can be used to stimulate both nerves and muscles within the body. One problem that is encountered, however, is that the applied electrical signals tend to spread widely, affecting untargeted muscles and nerves as well as targeted ones, which is often undesirable. Further, to account for this signal dissipation, the applied current levels must be significantly increased to ensure adequate current densities at the targeted site. Another challenge associated with transdermal application of electrical signals is the fact that some nerves are stimulated by a low frequency signal, such as the pudendal nerve which is stimulated by a frequency on the order of 10-40 Hz. Such a low frequency signal cannot itself pass through body tissue, and therefore is not conducive to direct transdermal application. Many of these challenges have been overcome by the devices described in detail below.

FIG. 1 illustrates schematically an exemplary transdermal signal transmission device 100 in accordance with the present invention. The signal transmitter is preferably contained within a transdermal patch 101 or the like that can be removably secured to the surface of the skin, preferably in the lower abdominal region or lower sacrum of the patient. The patch may be any suitable adhesive bandage or the like, such as the exemplary embodiment shown in FIG. 11 that will be described further below.

Figure 2A:
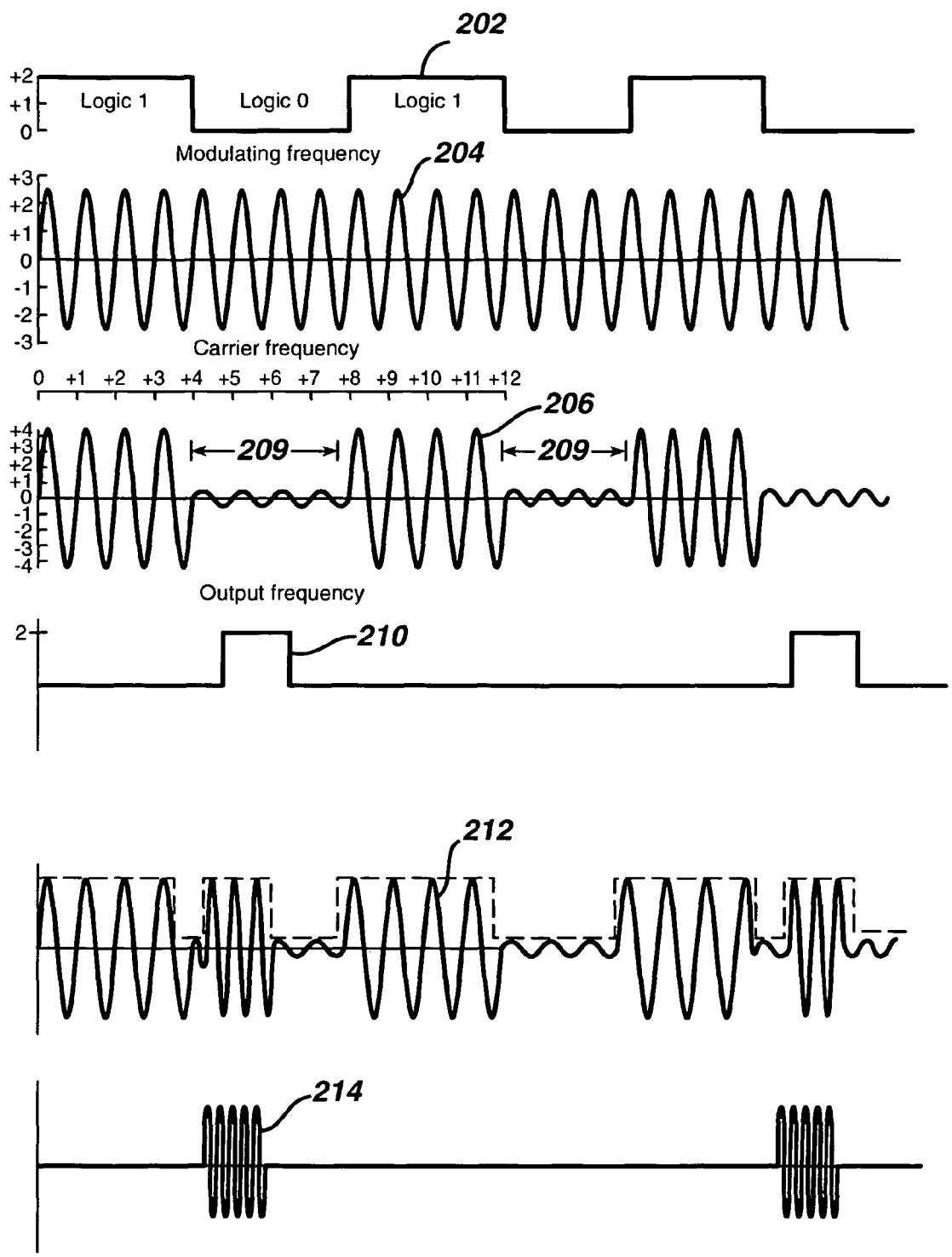
Figure 2B:
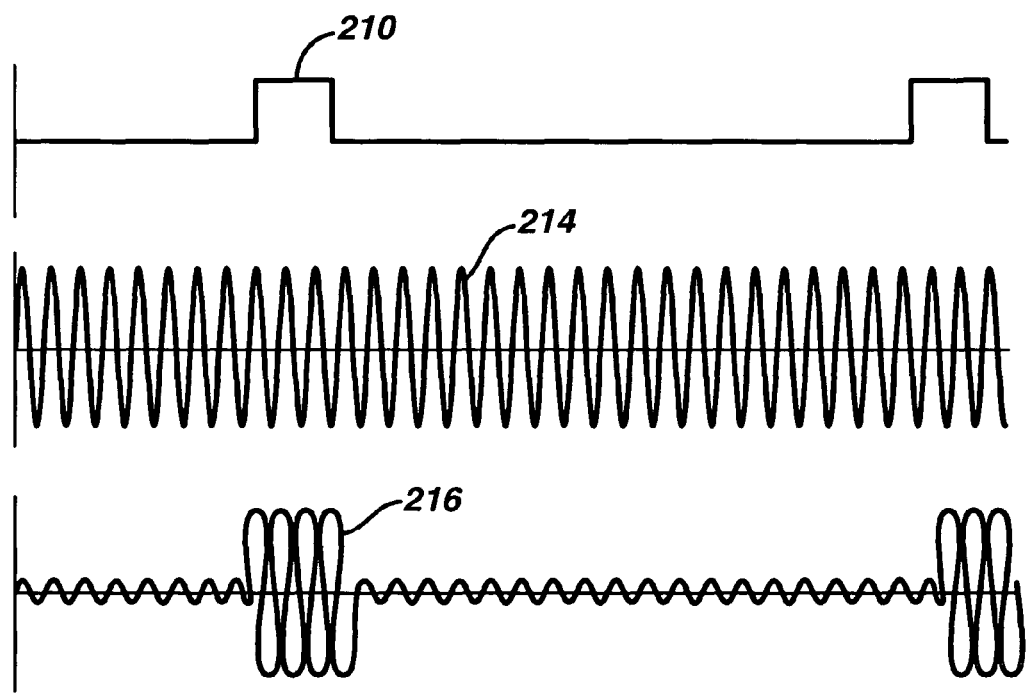

The signal transmitter 100 includes a suitable power source 102 such as a lithium ion film battery by CYMBE™ Corp. of Elk River, Minn., model number CPF141490L, and at least first 104, second 106 and third 107 waveform generators that are electrically coupled to and powered by the battery. These waveform generators may be of any suitable type, such as those sold by Texas Instruments of Dallas, Tex. under model number NE555. The first waveform generator 104 generates a first waveform 202 (see FIG. 2a) or signal having a frequency known to stimulate a first selected body part, such as the pudendal nerve, which is known to be stimulated by a frequency approximately within the range of 10-30 Hz. As indicated above, such a low frequency signal applied to the skin, in and of itself, cannot pass through body tissue to reach the pudendal nerve with sufficient current density to stimulate the nerve. Thus, the second waveform generator 106 is provided to generate a higher frequency carrier waveform 204, which is applied along with the first waveform to an amplitude modulator 108, such as an On-Semi MC1496 modulator by Texas Instruments. The first waveform is preferably a square wave having a frequency of approximately 10-30 Hz, and the second waveform is preferably a sinusoidal signal having a frequency in the range of 10-400 KHz. As those skilled in the art will readily recognize, modulation of this first waveform 202 with the second waveform (carrier waveform) 204 results in a modulated waveform or signal 206 having generally the configuration shown in FIG. 2a. The signals shown in FIGS. 2a and 2b are for illustrative purposes only, and are not intended as true representations of the exemplary signals described herein.

As described in detail in co-pending U.S. patent application Ser. No. 11/146,522, which is incorporated herein by reference in its entirety, this modulated signal 206 can be provided to an appropriate surface electrode 110, such as DURA-STICK Self Adhesive Electrodes from Chattanooga Group, Inc. of Hixson, Tenn., that applies the modulated waveform directly to the skin. As is readily understood by those skilled in the art, the use of the modulated signal enables transmission of the waveform through tissue due to the high frequency nature of the carrier waveform, yet allows it to be detected (and responded to) by the pudendal nerve due to the low frequency envelope of the modulated signal.

Rather than simply applying modulated signal 206 to selectively affect one nerve, the modulated signal 206 has periodic periods of inactivity 209 that can further be taken advantage of to generate a signal package capable of transdermally and selectively stimulating two or more nerves or other body parts. To accomplish this, a third waveform generator 107 generates a third waveform having a frequency different from the first waveform and that is specifically selected to stimulate a second nerve or body part. An exemplary third waveform 210 is shown in FIG. 2. This third waveform must be out of phase with the first waveform 202 to avoid interfering with modulated signal 206. Further, if the frequency ranges that simulate first and second nerves overlap, the third waveform can be generated or applied during the refractory period of the first nerve to ensure the first nerves inability to respond to this subsequent stimulus. The first 202, second 204 and third 210 waveforms are all applied to amplitude modulator 108, which modulates the three waveforms into a modulated signal package 212. The term "signal package" is used herein to describe a single output signal consisting or three or more individual signals modulated together in any way.

As indicated above, the first and third waveform generators generate their respective waveforms 202, 210 out of phase with each other so that when combined with the carrier waveform 204 they appear along separate and discrete portions of the signal package 212, and each of the first and third waveforms have a frequency selected to specifically target different nerves or body portions. For example, the first waveform 202 may have a frequency of 20 Hz, which is known to have an effect on the autonomic element branches of the pudendal nerve which is known to affect overactive bladder, and the third waveform may have a frequency of 10 Hz, which is known to have an effect on the somatomotor branch of the pudendal nerve that is useful in treating intersticial cystitis. To the extent there is an overlap in frequency ranges, the third waveform can be applied during the refractory period of the first nerve as previously stated.

By the system and method described above, individual components of the modulated signal package can be used to selectively target different nerves, different nerve branches, or selected other body parts. That is, a single patch could provide stimulation signals designed to relieve multiple different symptoms such as those associated with overactive bladder, fecal incontinence, interstitial cystitis and any other pelvic floor disorder.

Figure 1A:
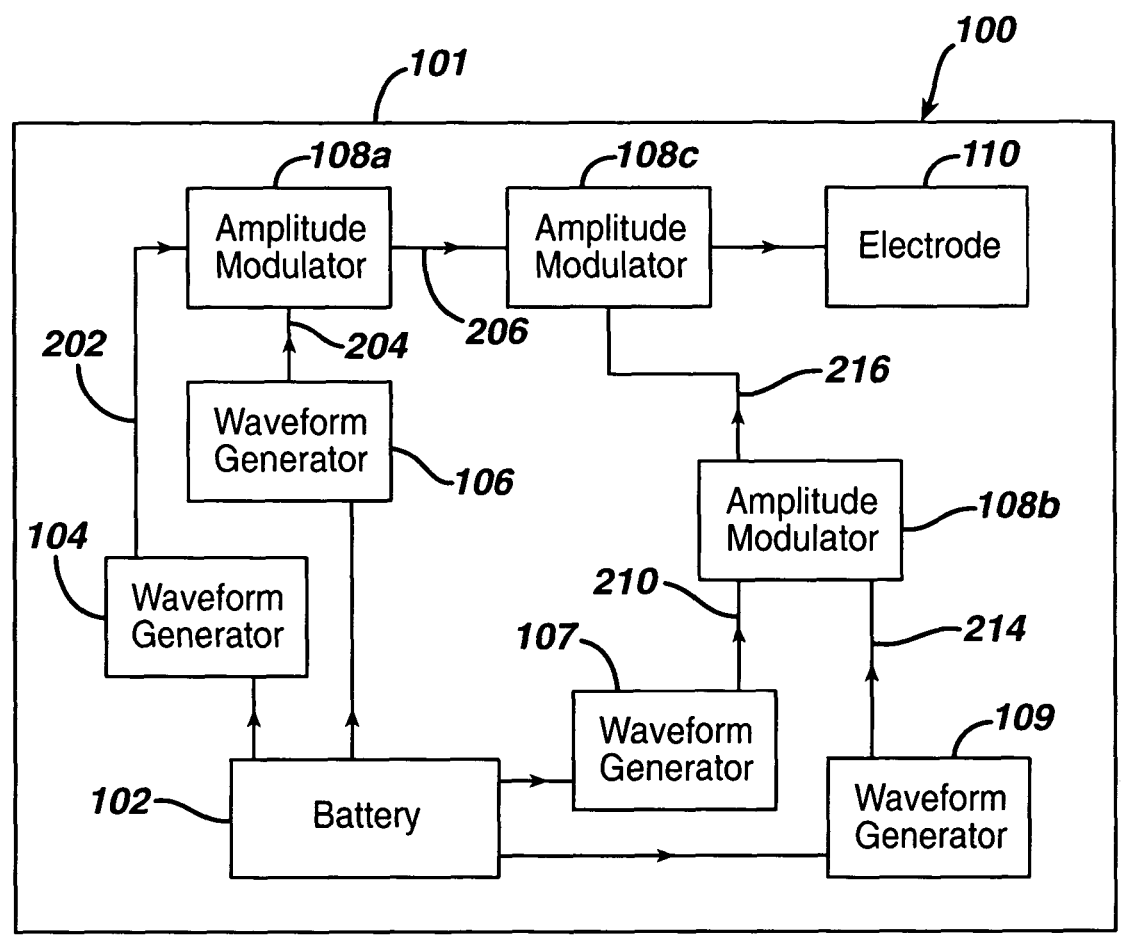

Although one specific embodiment has been described thus far, those skilled in the art will recognize that the appropriate signals may be manipulated in many different ways to achieve suitable modulated signals and/or signal packages. For example, a fourth waveform generator 109 may also be included that generates a fourth carrier waveform 214 having a frequency different from the second carrier waveform. This may be desirable if stimulation of the first and second nerve or body part will require the signal(s) to pass through different types or amounts of tissue. As illustrated, using a single amplitude modulator 108 the fourth carrier waveform 214 must be applied only during periods of inactivity of the first waveform to avoid affecting what would be modulated signal 206. In the alternative, as shown in FIG. 1a, the first waveform 202 and second carrier wave 204 may be provided to a first amplitude modulator 108*a* to result in a first modulated waveform as shown as 206 in FIG. 2*b*. Similarly, the third waveform 210 and fourth carrier waveform 214 may be provided to a second amplitude modulator 108*b* to result in a second modulated waveform 216 as shown in FIG. 2*b*. These first and second modulated waveforms may be further modulated by a third modulator 108*c* to create a signal package that can be transdermally applied by electrode 110. First and second modulated signals, of course, could also be applied separately via first and second electrodes.

As can be seen from signal package 212, there are still periods of the waveform that are not active. Additional signals can be inserted into these periods to target other frequency independent pudendal nerves or other body parts.

Figure 11:
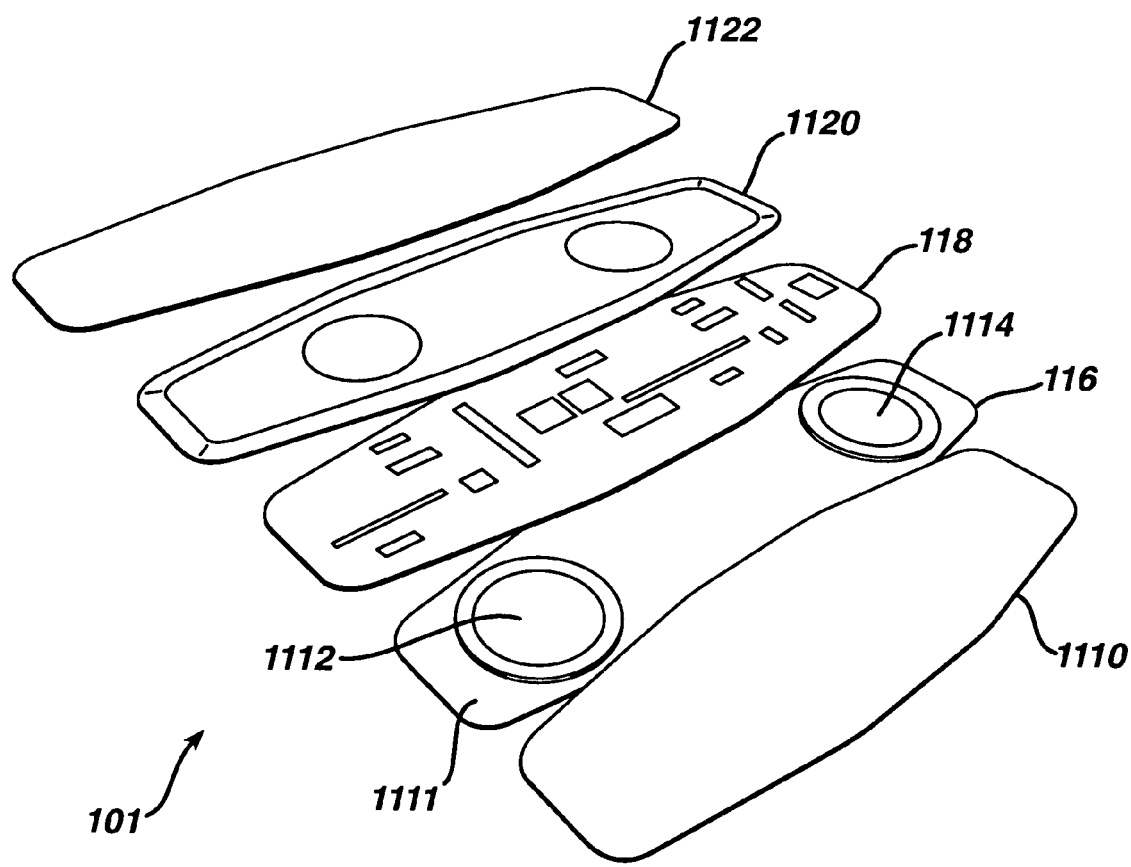
FIG. 11 illustrates one embodiment of a patch within which the devices of the present invention may be incorporated.

Referring now back to FIG. 11, the transdermal stimulation devices described herein may be incorporated into a transdermal patch 101. This patch may include a first layer 1110 having any suitable adhesive on its underside, with the active and return electrodes 1112, 1114 being secured to the top side 1111 of the first layer. The adhesive layer may further include holes therein (not shown) to accommodate the shape of the electrodes and allow direct contact of the electrodes with the surface of the patient's skin. The electrodes may be secured directly to the first layer, or may be held in place by a second layer 1116 comprised of any suitable material such as a plastic. A third layer 1118 consists of a flexible electronics board or flex board that contains all of the electronic elements described above and that is electrically coupled to the electrodes. A fourth layer 1120 is a thin film battery of any suitable size and shape, and the fifth layer 1122 is any suitable covering such as the plastic coverings commonly used in bandages.

Although capable of being applied transdermally only, the conductance of the stimulation energy from the surface electrode to the target nerve can be increased by the placement of a conductive pathway or "tract" that may extend either fully or partially from the surface electrode to the target nerve as illustrated by FIGS. 12*a*-12*c*. The conductive tract may be a cross-linked polyacrylamide gel such as the Aquamid® injectable gel from Contura of Denmark. This bio-inert gel, injected or otherwise inserted, is highly conductive and may or may not be an aqueous solution. The implanted gel provides benefits over rigid implants like wire or steel electrodes. Some of those advantages include ease of delivery, a less invasive nature, and increased patient comfort as the gel is not rigid and can conform to the patient's body. As stated above, the injected gel tract is a highly conductive path from the surface electrode to the target nerve that will further reduce energy dispersion and increase the efficiency of the energy transfer between the surface electrode and the target nerve. The conductive gel pathway may provide a conductive pathway from an electrode positioned exterior of the body (i.e., on the skin) or an electrode positioned under the surface of the skin, both of which are considered to be "in proximity" to the skin.

FIG. 12*a* illustrates an instance where the conductive gel tract 1201 extends from the transdermal stimulation device positioned on the skin 1200 of a patient to a location closer to the targeted nerve 1202 or nerve bundle. Another advantage of using such a gel material, however, is that unlike rigid conductors (wire), the gel can be pushed into foramina and other recessed areas. Wire or needle electrodes can only come in proximity to one plane of the target nerve, whereas the deformable and flowable gel material can envelope the target nerve as shown in FIG. 12*b*. That is, the gel tract can be in electrical and physical contact with the full 360 degrees of the target nerve, thereby eliminating conventional electrode alignment issues. Although described above as extending substantially from the transdermal stimulation device to a position closer to the target nerve, the conductive gel tract could also extend from a location substantially in contact with the target nerve, to a location closer to (but not substantially in contact with) the transdermal stimulation device. This type of configuration is illustrated in FIG. 12*c*. Multiple gel pockets or tracts in any configuration could be used.

Although one suitable conductive gel has been described above, various others are also suitable. Many thermoset hydrogels and thermoplastic hydrogels could be used as well. Examples of thermoset hydrogels include cross-linked varieties of polyHEMA and copolymers, N-substituted acrylamides, polyvinylpyrrolidone (PVP), poly(glyceryl methacrylate), poly(ethylene oxide), poly(vinyl alcohol), poly(acrylic acid), poly(methacrylic acid), poly(N, N-dimethylaminopropyl-N'-acrylamide), and combinations thereof with hydrophilic and hydrophobic comonomers, cross-linkers and other modifiers. Examples of thermoplastic hydrogels include acrylic derivatives such as HYPAN, vinyl alcohol derivatives, hydrophilic polyurethanes (HPU) and Styrene/PVP block copolymers.

The above-described signal transmission devices may also be used in a system that incorporates various biofeedback mechanisms to both create a closed-loop system for treating urge incontinence, but also to provide a system wherein pudendal nerve stimulation is selective, and applied only when necessary as opposed to constantly as has been the case with known attempts at pudendal nerve stimulation. Such a system further includes one or more sensor devices 115 that are preferably implanted within the body. The sensor devices preferably include at least one sensor 120 (FIG. 3) that will sense a selected bio-physiological property, and a data transmission device 122 that transmits data or information gathered by the sensor back outside the body to be further processed as described more fully below.

Figure 3:
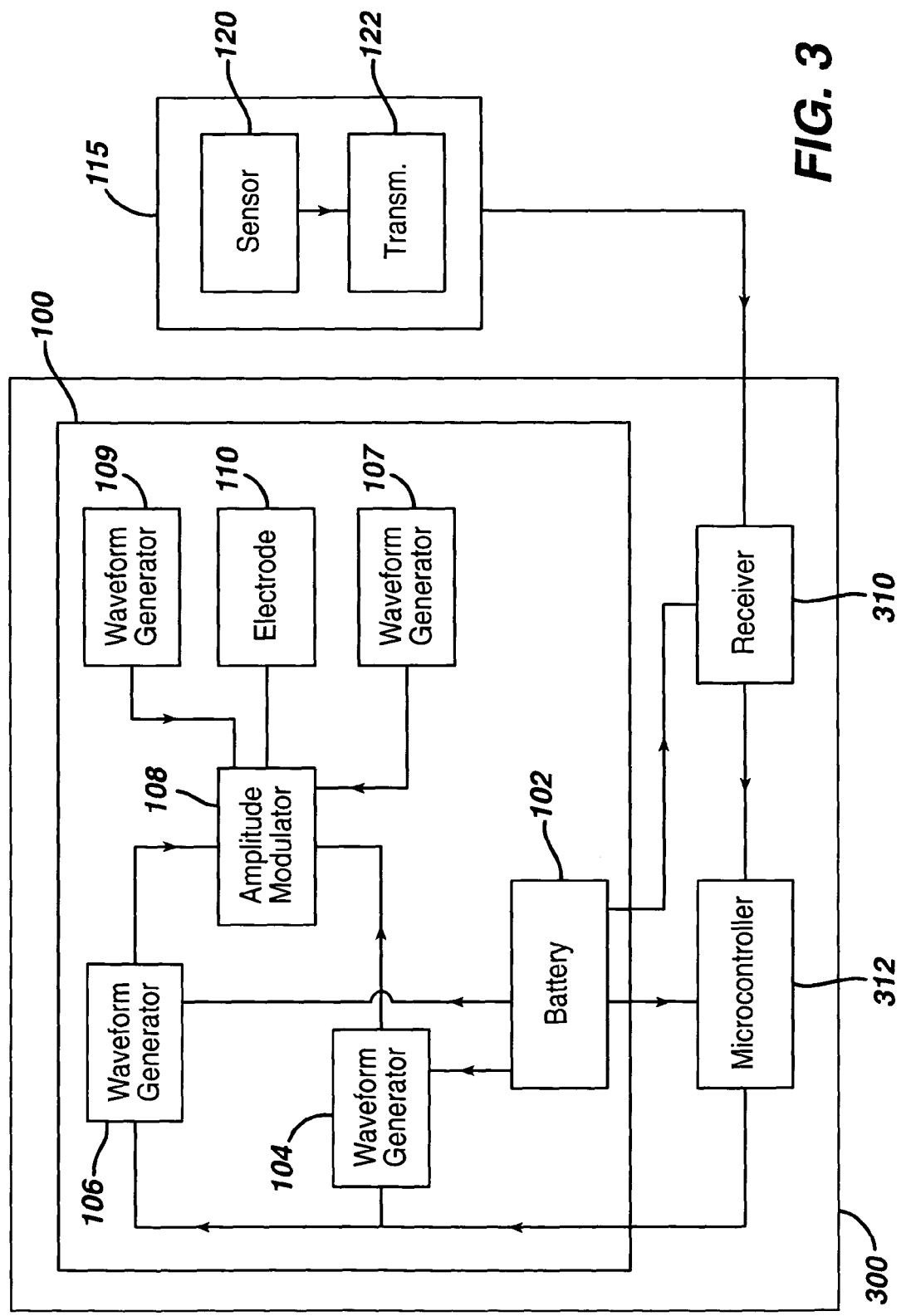
FIG. 3 is a schematic illustration of the device of FIG. 1 further incorporating a biofeedback mechanism.

Referring now to FIG. 3, signal transmitter 100 is part of a larger signal control device 300 that further includes a receiving device 310 such as a MAX1472 from Maxim Semiconductors of Sunnyvale, Calif., that is electrically coupled to and powered by the battery 102. The receiving device receives data from the one or more sensors 115 and provides this data to a microcontroller 312 or the like. The microcontroller is programmed to receive and analyze the data, and based on this data to provide input to the first and second waveform generators 104, 106 to thereby control signal transmission by the signal transmitter 100. For example, the biofeedback sensor 115 may be a pressure sensor that is implanted within the bladder as described in detail below. As pressure measured within the bladder over time is indicative of the existence and magnitude of bladder contractions, when such measurements indicate spastic bladder muscle activity (as compared to normal bladder contractions which will result in a slow and steady rise of pressure within the bladder), a feedback signal can be transmitted to the receiving device and subsequently to the microcontroller. Based on receipt of this signal, the microcontroller will, via control of the waveform generators, cause the electrode to transmit the modulated signal. Receipt of the signal by the pudendal nerve will innervate the bladder muscles to substantially eliminate the spastic muscle contractions.

Figure 4:
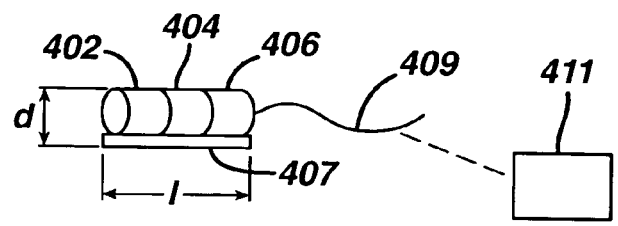
FIG. 4 illustrates an exemplary implantable sensor device that can be used in conjunction with the device of FIG. 3.
Figure 5A:
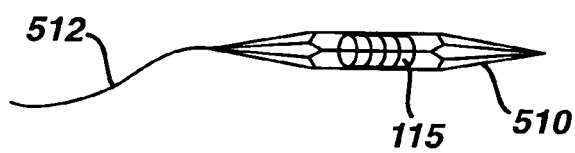
FIG. 5a illustrates the sensor device of FIG. 4 within an expandable cage in its non-expanded state.
Figure 5B:
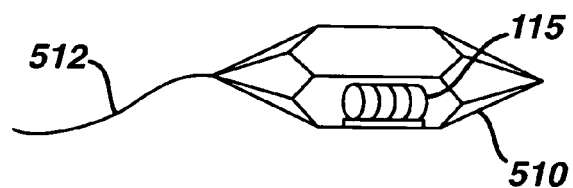
FIG. 5b illustrates the sensor device of FIG. 4 within an expandable cage in the expanded state.

Referring now to FIGS. 4, 5*a* and 5*b*, exemplary biofeedback devices 115 will now be described in greater detail. In a preferred embodiment, the implantable biofeedback device 115 consists of multiple electronic components including a power source 402, one or more sensor components 404, and an electronic interface 406, each of which are electrically coupled to one another and mechanically mounted on a printed circuit board 407 in a manner well known in the art. The one or more sensor components 404 sense predetermined physiological properties within the body, and transmit signals or data representing such properties to the electrical interface 406. The system may include a data storage element for storing data correlating to the sensed physiological properties, but may also include a transmitter 409 for transmitting the data external of the patient's body so that it can be used to control generation of the modulated signal as described above. As shown in both FIGS. 5a and 5b, in one embodiment the biofeedback device 115 is substantially surrounded by a collapsible housing 510 or cage.

Preferably, the biofeedback system (exclusive of the housing) has an overall size of about 0.65-10 mm in diameter d, and about 0.65-10 mm in length l. In a preferred embodiment, the sensor component is a micro-miniature piezo-resistive pressure transducer for measuring pressure within a patient's bladder. A suitable transducer is an MPX series pressure sensor from Motorola of Schaumburg, Ill. Other suitable components may include the MSP430F149 microcontroller from Texas Instruments, Inc. of Dallas, Tex. that can be used to acquire, filter and store data from the pressure sensor, and power source such as any suitable biocompatible lithium battery. Although particular suitable electronic components have been named above, many others also exist and could be incorporated into the present invention. As indicated, the electronic components are preferably mounted on printed circuit board. Subsequently, the components and circuit board can be covered or encapsulated in silicone or other suitable covering to protect them from the environment, such as the fluid environment in the bladder Referring now again to the housing 510 as illustrated in greater detail in FIGS. 5a and 5b, in a preferred embodiment the housing is a collapsible cage made of a suitable metal such as Nitonol, stainless steel, or a titanium alloy, or a suitable biocompatible polymer such as polypropylene or polyethylene terapthalate. The collapsible cage is advantageous in that it can exist in a collapsed state shown in FIG. 5a that is sufficiently small to allow insertion through the patient's urethra. Once inserted into the bladder as will be described further below, however, the cage can assume the expanded state shown in FIG. 5b, which has a size sufficiently large so that it cannot pass back into the urethra, and thus will remain in the bladder until physical removal is desired. The housing or cage returns to its expanded state (FIG. 5b) when not compressed by an external force. The electrical components and printed circuit board can be mechanically affixed to the cage in any suitable manner, such as by using a biocompatible adhesive. The housing may further include a tail element 512 extending outwardly therefrom. This tail element 512 may operate as the transmitter for the device in place of the transmitter configuration shown in FIG. 4. As will be further described below, this tail element 512 may also incorporate additional sensor elements if desired.

In another embodiment, the expandable cage may be made of an absorbable material such as Ethisorb® (an absorbable synthetic composite made from polyglactin and polydioxanone) from Ethicon, Inc. of Somerville, N.J., or a combination of absorbable and non-absorbable materials. The absorbable material would preferably dissolve after a predetermined period of time, such as at least 2-3 days, so that the implantable device could be used for temporary data acquisition and subsequently expelled from the body in a non-invasive manner after sufficient data has been gathered.

Figure 6:
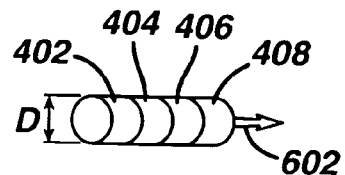
FIG. 6 illustrates an alternate embodiment of an implantable sensor device.

As an alternative to the collapsible cage described above, the housing could have a stable structure rather than a collapsible structure that itself has an outer diameter D that is smaller than the diameter of the urethra to allow insertion therethrough into the bladder (see FIG. 6). The housing may further have one or more projections 602, such as screw threads, barbs or the like, extending outwardly therefrom that can be attached to the sidewall of the bladder by being pushed or driven therein. In yet other alternate embodiments, the implantable device could be sutured to the bladder wall, or adhered thereto using a suitable biocompatible adhesive.

Figure 7A:
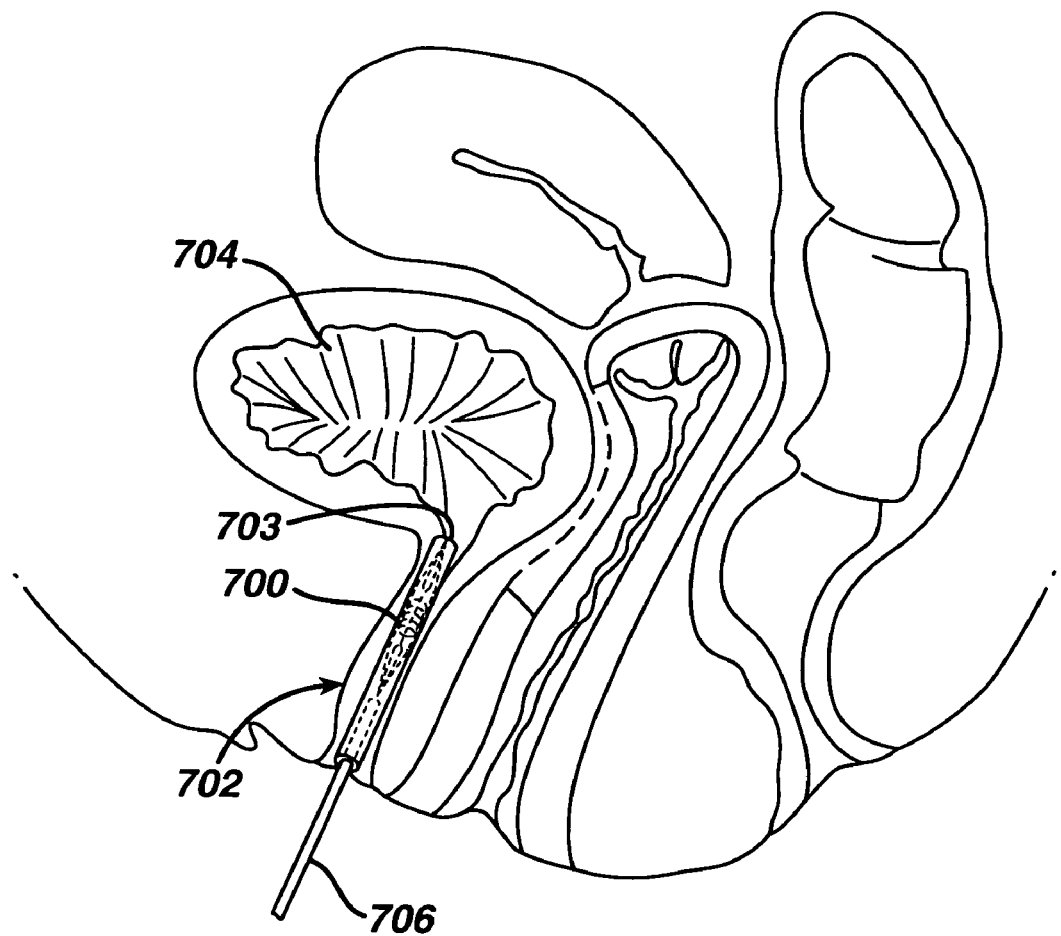
FIGS. 7a-7c illustrate various steps of deployment of the implantable sensor device of FIGS. 5a and 5b.
Figure 7B:
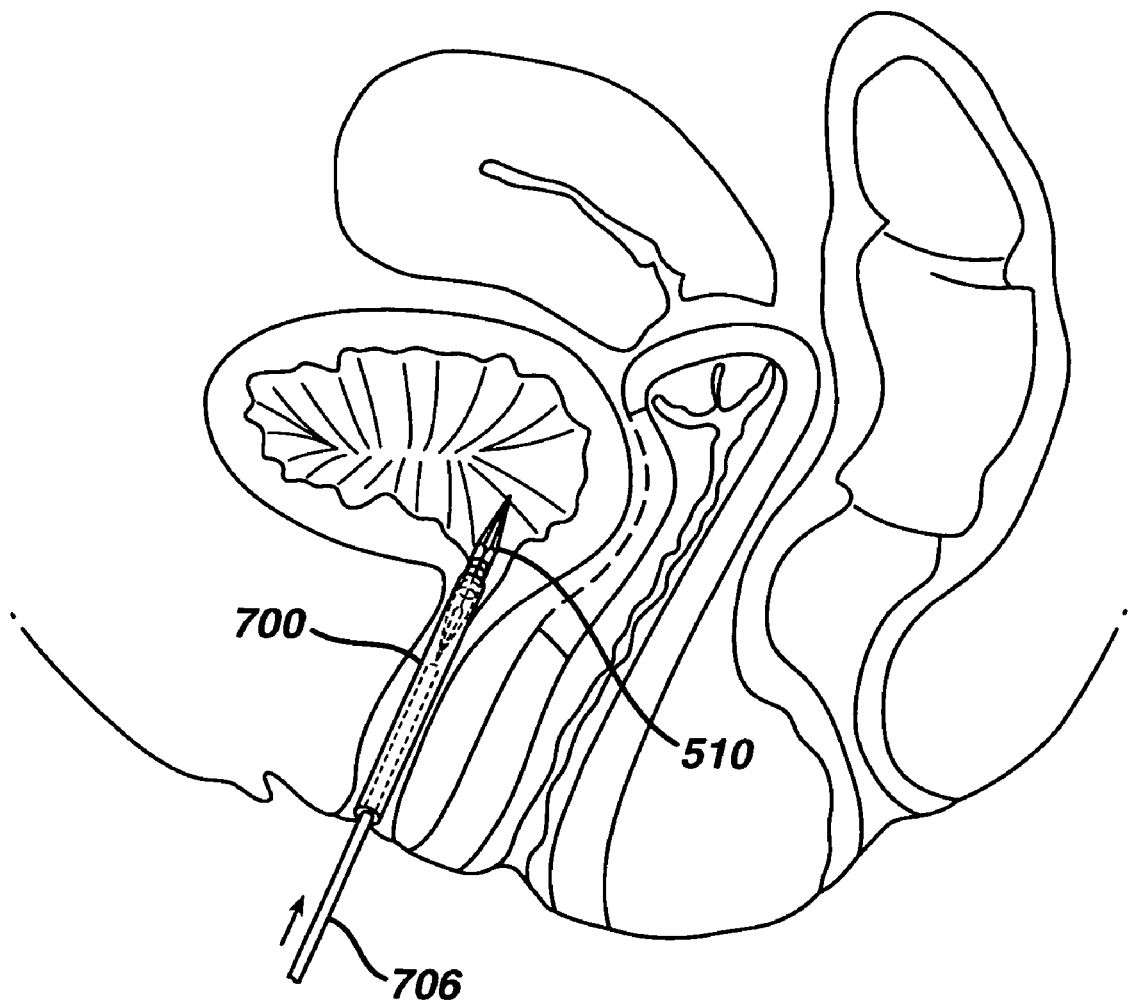
Figure 7C:
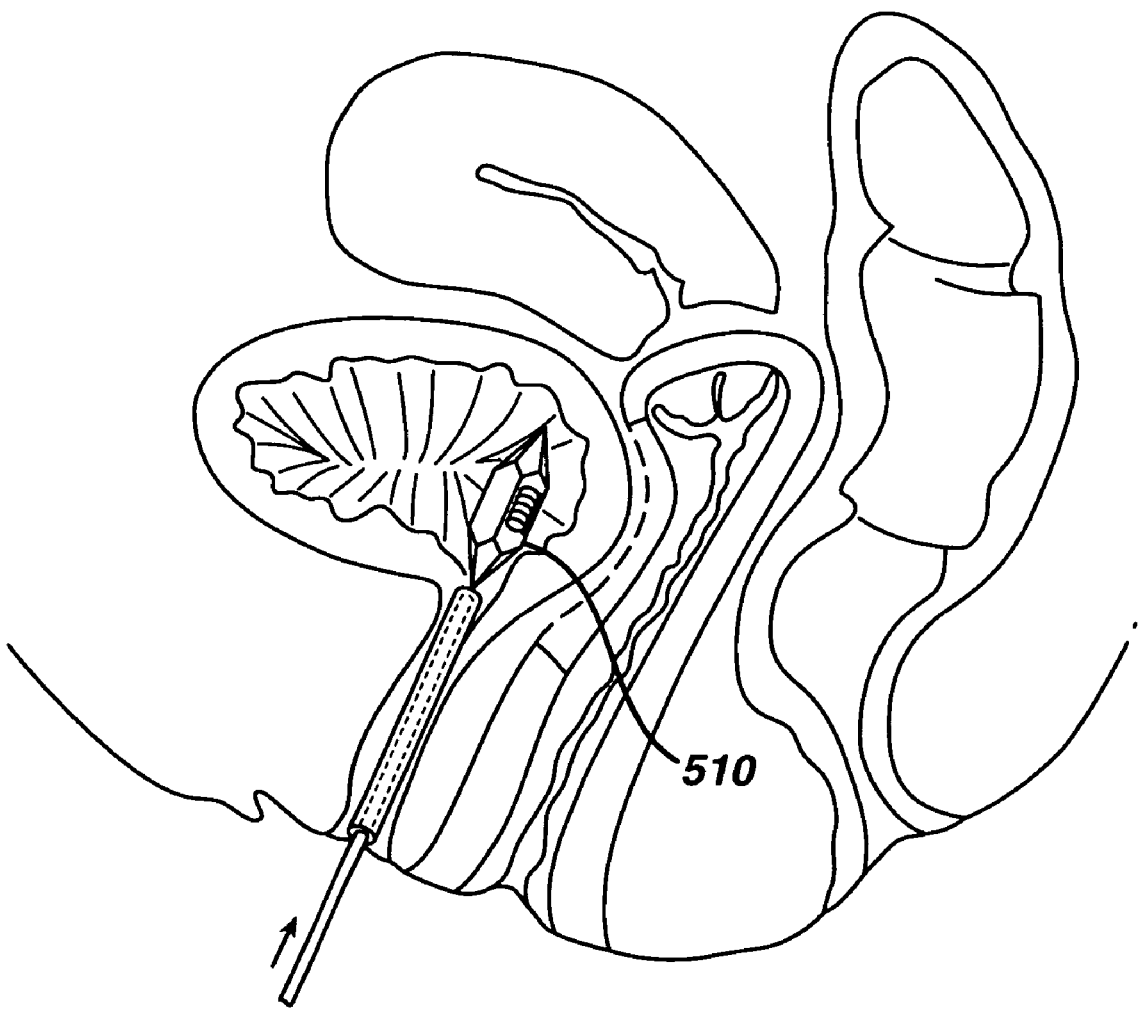
Figure 8:
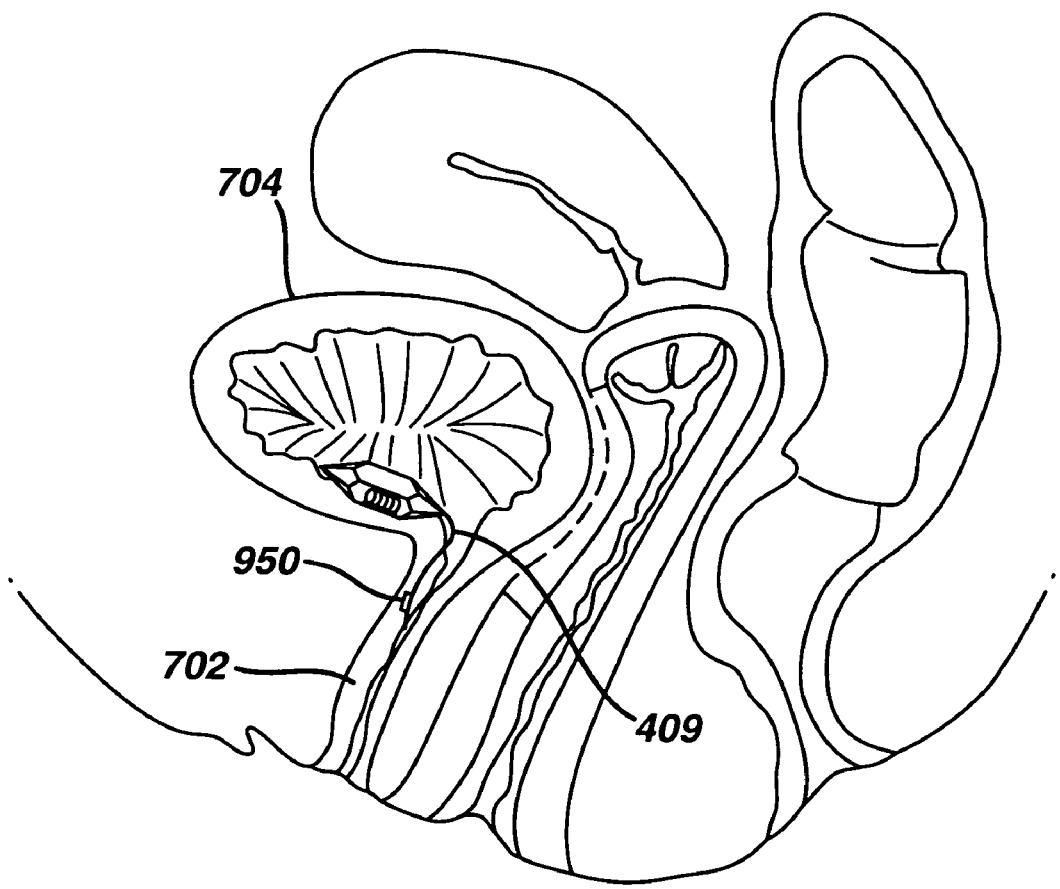
FIG. 8 illustrates the implantable sensor device of FIGS. 5a and 5b deployed within the bladder and having a tail extending into the urethra.

In order to implant the device 115, the housing 510 is compressed and loaded into a single or multi-lumen catheter 700 as shown in FIG. 7a, which is inserted through the urethra 702 until the tip or distal end 703 is positioned within the bladder 704. The catheter may be any catheter suitable for intra-urethral applications, such as a Foley catheter. Fluoroscopy, ultrasound or other similar technology known to those skilled in the art may be used to aid in delivery and placement of the implantable system within the bladder. If a multi-lumen catheter is used, other lumens may be used to fill or drain the bladder, deliver drugs, provide an access for visualization, or monitor pressure while placing the implantable system. An expulsion element 706, such as a push rod or the like is inserted into the primary lumen behind the device and housing, and once the distal end of the catheter is properly positioned within the bladder, the expulsion element is moved toward the distal end of the catheter in the direction of the arrow as shown in FIGS. 7b and 7c to thereby expel the device and housing from the distal end of the catheter and into the bladder. As the implantable system exits the catheter, the collapsible cage 510 is no longer being held in its collapsed state, and proceeds to expand to its fully expanded state. Although use of a catheter is described, other suitable implantation methods may also be used, such as placement via the working channel in a cystoscope or similar surgical tool, or placement via laparoscopic or open surgical methods. Once deployed within the bladder, the expandable cage is dimensioned to prevent the device from being lodged in the bladder neck or otherwise passing into the urethra, but further allows urine to freely flow through it. FIG. 8 illustrates the device fully deployed within the bladder 704.

As mentioned above, alternate embodiments that do not employ expandable cages may also be suitable, such as that shown in FIG. 6. The method of implantation of such devices would be similar to that described above, with the expulsion element within the catheter being used to drive the projecting element 602 into the wall of the bladder to thereby anchor the device to the bladder.

For purposes of the present invention, the device 115 would preferably remain within the bladder for an extended period of time to provide constant feedback used to control operation of the electrode. Where constant feedback is not used (i.e., FIG. 1), the implantable sensors described herein may nevertheless be used to obtain data useful in rendering an accurate diagnosis and/or appropriate treatment. For example, the device could remain within the bladder for 1-2 days, with bladder pressure measurements being taken every ½ second. The type and frequency of bladder pressure changes can be subsequently analyzed to provide feedback to assess urinary function. For example, vesicle pressure measured over time can reveal voiding times and frequency, can provide an indication of an overactive bladder, or of bladder overfilling. In one embodiment, the sensor element(s) are designed to operate in an extended sleep mode, "waking up" at fixed intervals of time to measure pressure or the like. Once sufficient data has been gathered, the device can subsequently be removed from the bladder by inserting a catheter into the bladder to retrieve the implantable device, or using the operating channel of a cystoscope or other suitable instrument to retrieve the device. The catheter or cystoscope would be inserted into the bladder, and the device grasped and pulled back into the catheter or cystoscope channel and subsequently removed from the body.

Under these circumstances, the biofeedback device may further incorporate a data storage device 408 (FIG. 4) in addition to or in place of the transmitter for storing rather than transmitting the data. The data can be subsequently retrieved and manipulated, preferably by uploading the data to a PC based software application in any suitable manner, such as wirelessly, for example, via an infrared data acquisition unit such as ENDEC HSDL-7001 and an IrDA transceiver HSDL-3202 interfaced to the microprocessor, via radiofrequency acquisition, or via a hard wire connection such as through an RS232 interface.

Figure 9:
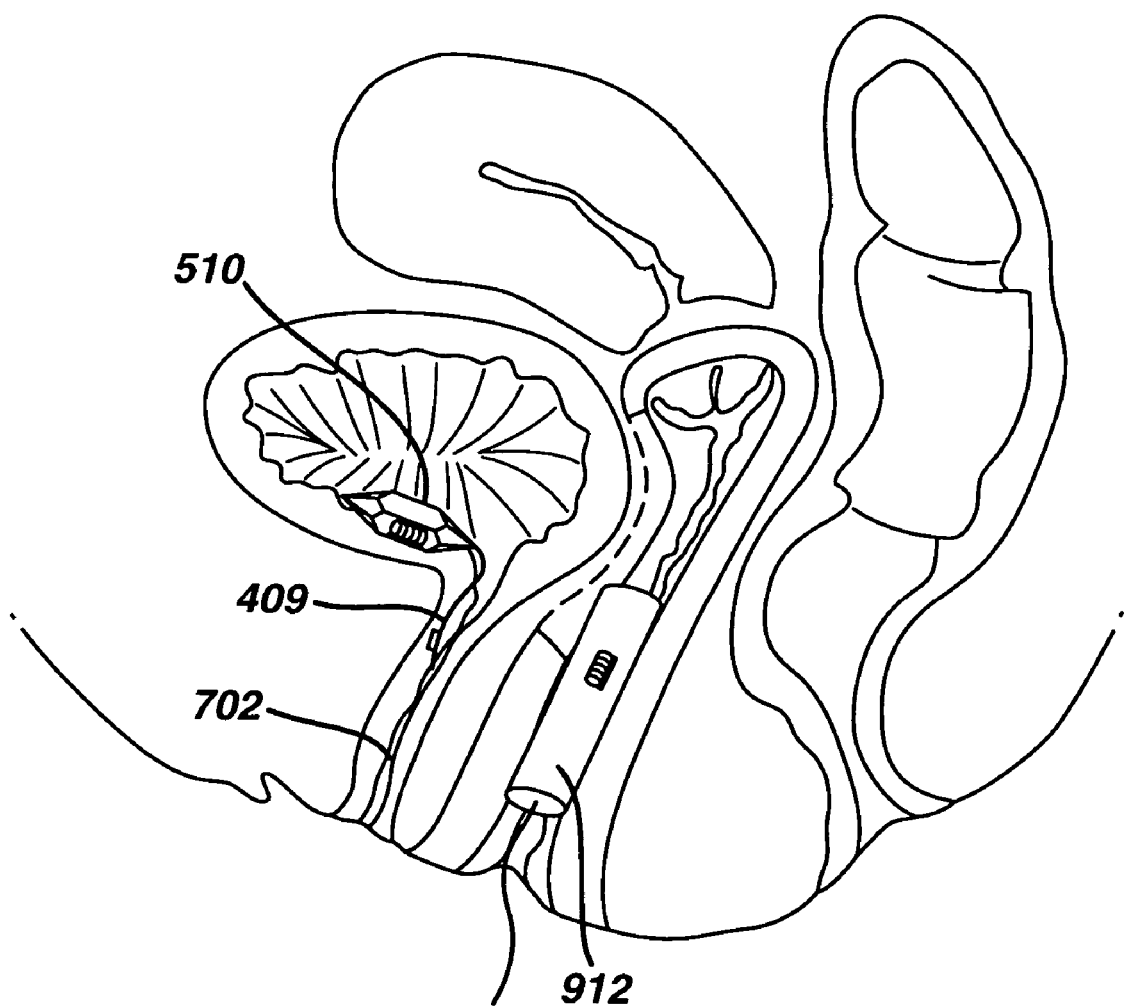
FIG. 9 illustrates first and second implantable sensor devices that can be used in conjunction with the system of FIG. 3.

Referring again to FIG. 3, where biofeedback data is utilized, receiver 310 may receive feedback data from more than one biofeedback device 115. In one embodiment shown in FIG. 9, a second implantable sensor device 902 similar to that shown and described in conjunction with FIG. 4 is designed for insertion into the vaginal canal of a patient, and thus is preferably encapsulated in a "tampon-like" device or casing as shown. This casing 912 is preferably simply rolled up or bound cotton, similar to a tampon. With the second implantable device sensing abdominal pressure, and the first implantable device sensing bladder pressure, the detrusor pressure (pressure of the muscle lining of the wall of the bladder tissue) can be determined by subtracting the bladder pressure from the abdominal pressure. Rises in detrusor pressure will occur if the patient strains, coughs, sneezes, laughs, etc., and detection of these pressures are clinically significant in the diagnosis of various bladder and lower urinary tract disease states. For example, the frequency of detrusor pressure increases provides meaningful data for assessing urge incontinence.

In an alternate embodiment, one of the two implantable devices transmits data to the other, which then wirelessly transmits both sets of data to receiver 310.

Figure 10A:
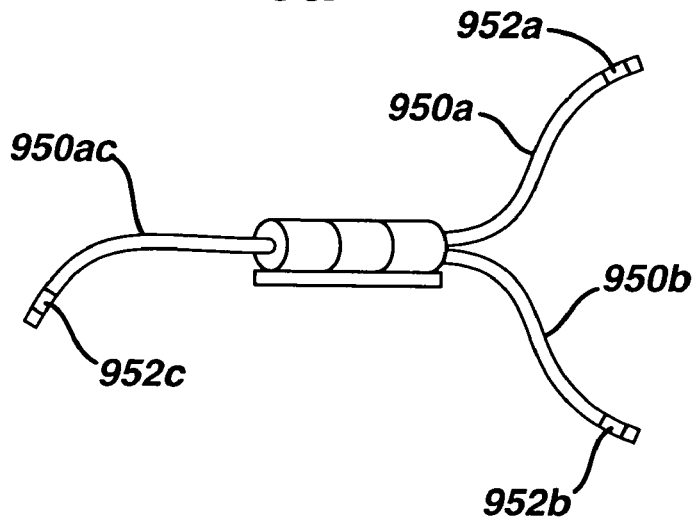
FIG. 10a illustrates an alternate embodiment of an implantable sensor device.
Figure 10B:
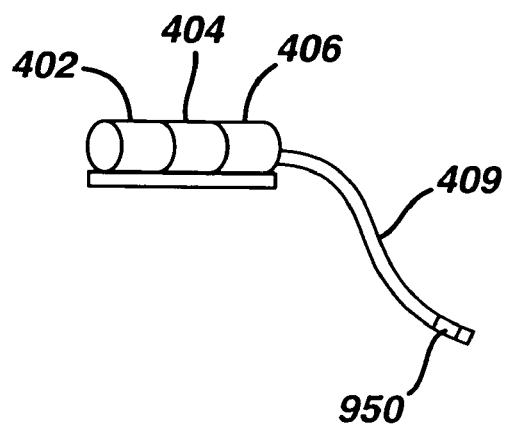
FIG. 10b illustrates yet another embodiment of an implantable sensor device.

In yet another embodiment, the first implantable device within the bladder further includes one or more additional sensors 950 that are incorporated into one or more tail elements, as shown in FIGS. 10a and 10b. In one particular implementation, the sensor(s) are leak detection sensors incorporated into a tail that is designed to extend from the device within the bladder, through the sphincter and into the urethral canal 702 as shown in FIG. 8. This sensor(s) detect the presence of fluid, and thus will detect leakage of urine such as occurs in a stress incontinent patient, while at the same time the pressure sensor within the bladder measures bladder pressure. Thus, stress incontinence episodes can be recorded by correlating time at which a rise in bladder pressure occurs concurrently with detection of fluid leakage through the urethra.

Further, multiple tail elements 950a, 950b, 950c may incorporate multiple sensor elements 952a, 952b, 952c as shown in FIG. 10a to record the pressure at different points in the bladder, and thus provide more accurate readings.

It will be apparent from the foregoing that, while particular forms of the invention have been illustrated and described, various modifications can be made without departing from the spirit and scope of the invention. Accordingly, it is not intended that the invention be limited, except as by the appended claims.

What is claimed is:

1. A transcutaneous electrical stimulation device for stimulating selected body parts of a mammal, comprising:
    a first waveform generator adapted to generate a first waveform having a first frequency capable of stimulating a first predetermined body part;
    a second waveform generator adapted to generate a second carrier waveform having a second frequency capable of passing through tissue of the mammal;
    a third waveform generator adapted to generate a third waveform having a third frequency different from and out of phase with that of the first waveform, and capable of stimulating a second predetermined body part;
    a modulation device electrically coupled to the first, second and third waveform generators and adapt to modulate the carrier, first and third waveforms to create a modulated signal package; and
    a first electrode electrically coupled to the modulation device and adapted to apply the modulated signal package thereto;
    wherein each of the first waveform, third waveform and the second carrier waveform are analog waveforms having a selected amplitude and frequency, and the modulation device is an amplitude modulation device configured to multiply the second carrier waveform, the first waveform and the third waveform to create the modulated signal package that maintains the amplitude and frequency information of the first waveform, third waveform and second carrier waveform.

2. The device according to claim 1, wherein the first, second, and third waveform generators and the electrode are positioned within a patch device having an adhesive thereon for securing the patch to the skin.

3. The device according to claim 1, further comprising a return electrode for receiving the signal package, wherein the first electrode and return electrode are both positioned relative to each other such that the applied signal package may pass from the first electrode to the return electrode substantially without passing through tissue of the mammal.

4. The device according to claim 3, wherein the first and second predetermined body parts are different nerves or different branches of a given nerve.

5. The device according to claim 4, wherein the first waveform has a frequency of approximately 20 Hz and the third waveform has a frequency of approximately 10 Hz.

6. The device according to claim 5, wherein the second carrier waveform has a frequency of approximately 10-400 kHz.

7. The device according to claim 5, wherein the first and third waveforms are square waves and the second carrier waveform is a sinusoidal wave.

8. The device according to claim 3, wherein the first and second predetermined body parts are the bladder and genitals respectively.

9. The device according to claim 1, further comprising a fourth waveform generator electrically coupled to the modulation device and adapted to generate a fourth carrier waveform having a frequency different than the second carrier waveform, and wherein the modulation device further modulates the fourth carrier waveform to create the modulated signal package.

10. The device according to claim 9, wherein the modulation device further comprises first, second and third modulators, wherein the first modulator modulates the first waveform and second carrier waveform to create a first modulated signal, and the second modulator modulates the third waveform and fourth carrier waveform to create a second modulated signal, and wherein the third modulator modulates the first and second modulated signals to create the modulated signal package.

11. The device according to claim 9, wherein the modulation device further comprises first and second modulators, wherein the first modulator modulates the first waveform and second carrier waveform to create a first modulated signal, and wherein the second modulator modulates the first modulated signal, third waveform, and fourth carrier waveform to create the modulated signal package, and wherein the fourth waveform generator generates the fourth waveform only during periods of inactivity of the first modulated signal.

12. A method for transcutaneously and selectively stimulating more than one body part within a mammal, comprising:
   identifying a first and second internal body parts for selective stimulation;
   generating a first waveform having a frequency capable of stimulating the first identified body part;
   generating a second carrier waveform having a frequency capable of passing through tissue of said mammal to reach the first and second identified body parts;
   generating a third waveform having a frequency capable of stimulating the second identified body part, the third waveform being generated out of phase with the first waveform;
   modulating the first, second carrier, and third waveforms to create a modulated signal package; and
   applying the modulated signal package substantially to a skin surface of said mammal;
   wherein each of the first waveform, third waveform and the second carrier waveform are analog waveforms having a selected amplitude and frequency and the modulating step is amplitude modulation for multiplying the second carrier waveform, the first waveform and the third waveform to create the modulated signal package that maintains the amplitude and frequency information of the first waveform, third waveform and second carrier waveform.

13. The method according to claim 12, wherein the modulating step further comprises first modulating the first waveform and second carrier waveform to create a first modulated signal, and subsequently modulating the first modulated signal with the third waveform.

14. The method according to claim 12, further comprising generating a fourth carrier waveform having a frequency different than the second carrier waveform, wherein the modulating step comprises the steps of modulating the first waveform and second carrier waveform to create a first modulated signal, and modulating the third waveform and fourth carrier waveform to create a second modulated signal.

15. The method according to claim 14, wherein the modulating step further comprises modulating the first and second modulated signals to create the modulated signal package.

* * * * *